United States Patent [19]

Shields

[11] Patent Number: 5,658,256
[45] Date of Patent: Aug. 19, 1997

[54] UNIVERSAL SHARPS SHIELD

[76] Inventor: Jack W. Shields, 1950 Las Tunas Rd., Santa Barbara, Calif. 93103

[21] Appl. No.: 643,184

[22] Filed: May 3, 1996

Related U.S. Application Data

[63] Continuation-in-part of Ser. No. 293,798, Aug. 22, 1994, Pat. No. 5,549,568.

[51] Int. Cl.$^6$ .................................................. A61M 5/32
[52] U.S. Cl. ................................... 604/192; 604/263
[58] Field of Search ............................. 604/263, 192, 604/198, 199, 187

[56] References Cited

U.S. PATENT DOCUMENTS 5,549,568   8/1996   Shields ........................... 604/192

*Primary Examiner*—John D. Yasko

[57] ABSTRACT

I describe a an elastomeric tube whose leading end holds a tubular puncture-resistant needle shield by means of elastic recoil and whose trailing end attaches by elastic recoil to the conical hub of a hollow needle. A removable cylindric hub-cap initially covers the elastomeric tube surrounding the needle. The purpose of the assembly is to sustain needle sterility after filling from a vial and before use in a patient, as well as to prevent accidental needle sticks after use in a patient. The user attaches the tubular assembly to a Luer-Lok on a syringe or onto the leading end of tubing used for transferring fluids. He/she removes the cylindric hub-cap and inserts the needle tip into a penetrable vial cap for filling and later discharge into a patient, another vial or a capped IV infusion port. The tubular needle shield slides back over the shaft of the needle with penetration of skin or a capped vial surface, while the elastomeric tube shortens like an accordion. When the user retracts the needle from the capped vial or from a patient, elastic recoil in the tube causes the conical needle shield to slide back and automatically re-shield the exposed shaft and beveled tip.

4 Claims, 1 Drawing Sheet

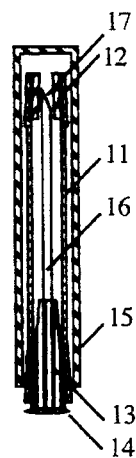 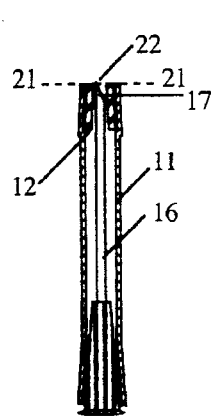 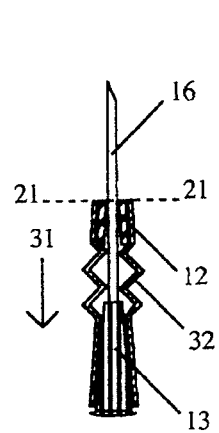 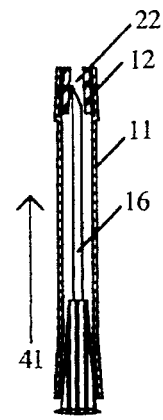
Fig. 1    Fig. 2    Fig. 3    Fig. 4
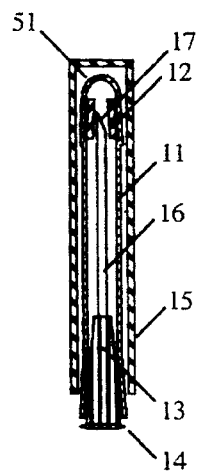 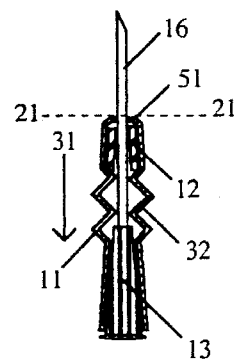 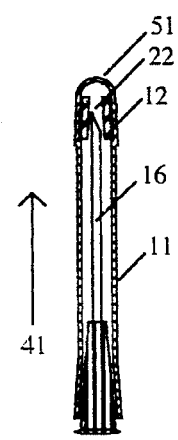
Fig. 5    Fig. 6    Fig. 7
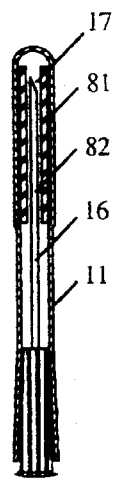 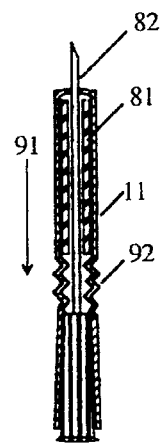 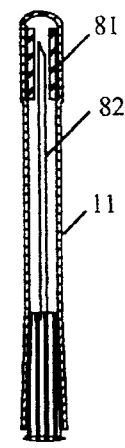 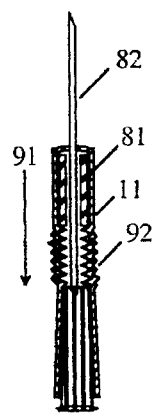
Fig. 8    Fig. 9    Fig. 10    Fig. 11

UNIVERSAL SHARPS SHIELD

This application is a continuation-in-part of Ser. No. 08/293,798 filed Aug. 22, 1994 now U.S. Pat. No. 5,549,568.

FIELD OF THE INVENTION

This invention relates to the sterile protection of a hollow bore needle before use in a patient and prevention of accident needle sticks following use. An object is to prevent contamination of the needle surface before use and finger access to the needle tip after use.

DESCRIPTION OF PRIOR ART

In order to prevent accidental needle sticks to health care workers in situations where the bore of the needle might contain blood-borne pathogens, especially viruses which cause AIDS or hepatitis, a variety of devices have been designed. Many of these do not protect the shaft or bevel of the needle from contamination by skin- water- or air-borne pathogens.

Most of the devices for protecting health care workers (HCW) from accidental needle sticks depend on sliding a puncture resistant cylinder beyond the sharp tip of a hollow-bore steel needle or pulling the needle within a cylindric holder so that access to the sharp tip is precluded by locking mechanisms after a single needle use. Such devices are usually provided with spring mechanisms or manual means which retract the needle into a guarded and locked position. In general, these devices leave considerable space beyond the tip of the needle because the diameter of the protective cylinder is large in comparison with the diameter of the needle. Characteristically, the diameter of the cylinder exceeds the diameter of the needle hub, of tubing trailing the needle hub or of a syringe to which the needle hub is attached. Because such devices do not depend on the use of elastomers or cones, they will not be reviewed in detail.

The use of elastomeric caps over needles is standard in Vacutainer™ systems wherein a latex cap covers the trailing end of a double-ended needle inserted into a holder. The latex cap prevents blood spillage into the holder from the trailing end of the needle, but provides no protective features for the sharp needle tip which is customarily well-protected until detachment of the needle hub from a cylindric holder for a vacuum vial.

Shields disclosed in U.S. Pat. No. 4,932,946 Jun. 12, 1990) and in U.S. Pat. No. 5,061,250 (Oct. 29, 1991) a slit elastomeric tube attached to the hub of a needle for safely covering the needle tip by means of a cylindric guard. The needle is exposed and recovered by stretching and bending the elastic tube such that the needle passes through the slit. These disclosures are pertinent, but not applicable to the instant invention which claims no slit.

Sims disclosed in U.S. Pat. No. 4,846,809 Apr. 11, 1989) a needle tip protective device comprising a collapsible sleeve disposed about the shank of a needle with a protective cap located at one end to enclose the sharp point of a needle. A sealing member in the device permits exposure of the needle when pushed through. The device was claimed to spring back to re-enclose the needle tip after use to protect HCW, but provided insufficient space between the collapsible sleeve and the needle shank to collapse and extend efficiently.

Kuracina et al disclosed in U.S. Pat. No. 4,998,922 Mar. 12, 1991) a device consisting of a needle hub-attached, spring-operated plastic tube with four longitudinal slits for safely covering and automatically recapping the tip of a hollow-bore steel needle. Lacking springs and slits, the instant invention differs structurally, although the purpose for protecting the needle tip is similar. Although surfaces between slim prevent finger contamination of the needle shaft before use, the slits do not prevent access of microorganisms.

The instant invention is unique in the fact that functional use depends entirely on the properties of an elastomer, such as silicone or latex, to return to its molded shape after compression, stretching or bending. The elastomeric tube described herein is stretched over a rigid object at each end, such that it holds each securely each by means of elastic recoil. Intervening parts of tube not stretched or confined by inside or outside objects remain capable of compression and bending when an axial force is applied, and will automatically resume the original shape when this force is released.

SUMMARY OF THE INVENTION

The object of this invention is to provide simple, efficient and inexpensive means for maximizing sterility of hollow-bore needle before use and for preventing accidental needle stick injuries from the needle tip to HCW after use.

Usage is structurally limited to syringes, Vacutainers™ and trailing tubing wherein needle insertion into a patient or into a container is straight in and straight out in the long axis of the hollow needle. Where needle insertion needs to be oblique, as in venous access, use is not recommended.

BRIEF DESCRIPTION OF THE DRAWINGS

FIG. 1 is a diagrammatic coronal section in the long axis of the needle showing a needle hub-cap over the elastomeric tube and needle hub. (Scale 1:1).

FIG. 2 is a similar section with the needle hub-cap removed and the needle advanced almost to the leading opening of the elastomeric tube.

FIG. 3 is a similar section with the elastomeric tube pushed back as a result of needle entry into penetrable skin or into a container with a penetrable cap.

FIG. 4 is a similar section showing the elastomeric tube automatically re-extended.

FIG. 5 is a section similar to that in FIG. 1 showing a closed leading end on the elastomeric tube.

FIG. 6 is a section similar to that in FIG. 3 showing the closed leading end of the elastomeric tube under pressure from a flat needle-penetrable surface.

FIG. 7 is a section similar to that in FIG. 4 showing the closed leading end of the elastomeric tube after pressure has been released.

FIG. 8 is a section similar to that in FIG. 5 showing a long enclosed tubular shield.

FIG. 9 is a section like that in FIG. 5, showing the effects of a long enclosed shield on needle exposure with axial compression of the elastomeric tube.

FIG. 10–11 are sections comparable with those in FIGS. 8–9, showing the effects of a short tubular shield on needle exposure with axial compression of the elastomeric tube.

DESCRIPTION OF PREFERRED EMBODIMENTS

As shown in FIG. 1, the device consists of an elastomeric tube 11 containing a rigid cone 12 inserted into its leading end. The small leading end of the cone 12 is almost flush with the leading end of the elastomeric tube 11 and has an external diameter nearly equal to the internal diameter of the elastomeric tube 11. The external diameter of frustum of the cone 12, being larger in diameter than the internal diameter of the elastomeric tube 11, is held by elastic recoil in the leading end of the elastomeric tube. The trailing end of the elastomeric tube 11 affixes by stretching to the leading end of a conical needle hub 13 whose external diameters are progressively greater than internal diameter of the elastomeric tube 11. Between the trailing end of the elastomeric tube 11 and trailing flanges 14 on a needle hub 13, sufficient space is left such that the over-riding elastomer will not interfere with customary flange action within a Luer-Lok (not shown). Instead of a standard conical needle sheath normally supplied with a hollow-bore steel needle, a puncture-resistant substantially cylindric needle hub-cap with a closed leading end 15 slip-connects over the elastomer covering the leading end the needle hub 13 to form an air-tight reversible connection and encloses the entire length of the elastomeric tube 11 and contents without binding.

The length of the elastomeric tube 11 is determined by the length of a hollow needle 16 exposed beyond its needle hub 13. The bore of the elastomeric tube 11 is equal to or smaller than the leading external diameter of the inserted cone 12 and smaller than the leading external diameter the conical needle hub 13. The thickness can vary with material durometer and size of the inserted cone 12. The dimensions of the inserted cone 12 depend, in turn, on the gauge of the hollow needle 16 held by the needle hub 13 and the length of the needle bevel 17.

The length of the inserted cone 12 should be approximately 1.5 times the internal diameter of the elastomeric tube and should be adjusted such that the leading tip of the needle 16 trails the leading opening by a distance at least equal to the length of the needle bevel 17. The internal diameter of the cone 12 at its leading end should be slightly larger than the external diameter of the needle and the same or larger at the trailing end. The external diameter of the inserted cone 12 at its leading end should be equal to or slightly greater than the internal diameter of the inserted elastomeric tube 11; and should be substantially greater at the trailing end, such that the constituent elastomer must stretch over the frustum which retards displacement in a trailing direction. The material of the inserted cone should be rigid and resistant to puncture by the sharp tip of a hollow-bore steel needle.

As shown in FIG. 2, the cylindric needle hub-cap 15 has been removed and the leading end of the sterile assembly has been advanced against a flat surface depicted by a dotted line 21—21. The leading tip of the hollow needle 22 is ready to penetrate and use for giving a subcutaneous injection, for retrieving fluid from a vial with a flat cap, or for conveying fluid to or from a container with an appropriate nipple having a flat surface. It should be noted that forward movement of the needle for a distance as small as the length of the needle bevel compresses the elastomeric tube, but produces little visible distortion.

It should be noted further that the shaft 16 and bevel 17 of the hollow needle are covered such they can not be contaminated by touching. The sharp tip 22 of the needle 16 is recessed by a distance equal to or longer than the beveled tip and exposed through a leading aperture in the cone 12 only slightly larger than the external diameter of the needle of selected gauge.

As shown in FIG. 3, when the leading end of the needle 16 is inserted straight through the skin, a vial cap or nipple of a container, depicted by the plane 21—21, the trailing end of the cone 12 will compress the elastomeric tube against the leading part of the needle hub in the direction of the arrow 31 such that tube assumes a shortened accordion-like shape 32. This allows the leading two-thirds of the needle 16 to be used effectively for intended purposes already described.

As shown in FIG. 4, when the needle 16 is withdrawn from the intended site of usage, the elastomeric tube 11 will return to its original shape in the direction of the arrow 41. As a result, the leading tip 22 of the needle 16 will be re-enclosed in the puncture-resistant cone 12. Thus, in practice, the user will find it difficult to stick himself/herself intentionally or accidentally with the leading tip of the needle, unless stuck straight on at an angle of 90 degrees.

In operation, the user employs this assembled device like a standard hub-attached hollow-bore needle with a sharp leading tip. He/she attaches the needle hub to a standard Luer-Lok or uses one pre-attached to tubing or the trailing end of a Vacutainer™ needle. After removal of the outside cylindric hub-cap from the leading end of the needle hub, everything is the same. However, the user will find it impossible to touch the needle shaft and difficult to touch the needle tip before use. After use, he/she will find the needle automatically re-shielded and simple to dispose of conveniently, either directly into a sharps container, or into a conical syringe/needle shield which facilitates single-handed recapping of the needle and leading end of the syringe, as described in U.S. Pat. No. 5,xxx,xxx. [allowed Feb. 6, 1996].

The user will find it difficult to use this device under conditions where the needle must be inserted into a receptive surface at an angle of less than 75°, unless he/she retracts the trailing end of the elastomeric tube to expose the leading end of the needle before insertion into the skin or into a container. Thus, the assembly is not recommended for intravenous access.

A second and preferred embodiment with a closed leading end 51 on the elastomeric tube 11 is shown in FIGS. 5–7. As shown in FIG. 5, the rigid cone 12 is inserted into the leading end of the elastomeric tube 11 to the point where the elastomer narrows in diameter to form a rounded closed end 51. Position of the needle bevel 17 in the rigid cone 12 should be as already described with a leading space approximately equal to the length of the beveled tip 17 of the needle 16 in the leading end of the rigid cone 12. It should be noted that the needle 16 within the elastomeric tube 11 can be expected to remain untouchable and air-tight after the cylindric hub cap 15 is removed, because the leading portions and trailing portions of the elastomeric tube are closed.

As shown in FIG. 6, when the needle 16 penetrates a flat surface 21—21 after passing through the rounded closed end 51 of the elastomeric tube 16, the closed end 51 will be compressed against the leading end of the rigid conical needle shield 12 whose posterior displacement within the elastomeric tube 16 is prevented by its wide trailing frustum.

As shown in FIG. 7, after the needle 16 has been withdrawn from the flat surface, the rounded closed end 51 of the elastomeric tube 11 will assume its original shape and, depending on the gauge of the needle 16, seal the path of the needle through the rounded closed end 51. Thus, leakage from the bore of the needle outside of the elastomeric tube 11 will be minimized.

Because maintaining needle sterility before use and preventing fluid leakage after use are important considerations, the preferred version of the elastomeric shield is shown in FIGS. 5–7. This is more complex to manufacture, because it requires elastomeric molding, as opposed to cuffing tubing to specified lengths and inserting a conical or tubular shield of specified length. As shown in FIGS. 8–11, the length of the inserted shield inversely determines the length of needle shaft 82 which will be exposed beyond the confines of the elastomeric tube 11. For instance, FIGS. 8–9 show that when a long tubular shield 81 is contained in the elastomeric tube 11, and pressure against the leading end from a surface is exerted in the direction of the arrow 91, only a short segment of the shaft 82 will be exposed. FIGS. 3, 6, 10–11 show the opposite, i.e. a short tubular shield permits exposure of a long segment of shaft 82, as the elastomer 11 shortens and compresses into folds 92 which limit posterior excursion of the shield 81 in the direction of the needle hub.

In effect, this inverse relationship between the shield length and outward thrust of the needle shaft is useful in gauging the depth for an intended injection, such as subcutaneous or intramuscular, or usage of the conical needle shield for transferring medications from one capped vial to another, or from a capped vial to a capped infusion port in a standing intravenous infusion port. In the latter usage, it would be wise to so shield a non-coring, instead of a standard beveled needle. In the former usage, wherein health care workers are giving injections into patients, or patients, such as diabetics, are obliged to give injections to themselves, the capacity to pre-select the depth, as well as maximize sterility, would seem advantageous.

As shown in FIGS. 1–7, the tubular shield 12 can be essentially conical in shape; or in the form of a cylinder 82, as shown in FIGS. 8–11. In either case, the effect of axial compression of the elastomeric tube against the conical leading end of the needle hub tends to push the tubular shield forward, thus further recessing the leading tip 22 of the needle 16 into the puncture resistant tubular shield 12, 82.

Finally, it should be mentioned that the cylindric hub cap 15 specified for covering the elastomeric needle shield before use is not essential to the specifications or usages enumerated. However, like the conical scabbards customarily supplied on hollow-bore steel needles, the cylindric hub cap is essential for maintenance of sterility and user protection before use, whether the hub-cap and elastomeric needle shield is supplied as a separate packaged unit, or supplied as a unit attached to a sterile packaged syringe.

Whereas the foregoing specifications are provided to instruct in fabrication and efficient medical uses of the invention, persons familiar with the art should recognize that the scope of the invention should not be limited to the structure/and functional specifications cited.

Therefore, I claim:

1. A widely applicable conical sharps shield for reversibly and safely enclosing a variety of manually operated, inserted sharp instruments, each having a sharp leading end, a body larger in diameter and greater in length than the sharp leading end, and a trailing end manipulated by fingers, said conical sharps shield comprising a hollow cone with:

a. a puncture-resistant consistency, preferably less rigid than the consistency of body of the sharp instrument for increasing the frictional area of surface contact when force is applied during insertion of a sharp instrument into said hollow cone;

b. an open apex of variable size, c. an open frustum having a trailing internal diameter greater than the greatest external diameter of the body of the insertable sharp instrument, d. a hollow body between said open apex and said open frustum, said hollow body having:

i. an axial length approximately equal to or less than the combined axial length of the sharp end and the body of the sharp instrument, ii. an apical internal diameter smaller than said greatest external diameter of the body of the sharp instrument, iii. an internal diameter which gradually reduces in size from said frustal internal diameter to said apical internal diameter, such that insertion of the sharp instrument through said open frustum into said hollow body to the point where said greatest external diameter the body of the sharp instrument and the internal diameter of said hollow body become equal will create a wedge impaction which leaves the leading sharp end of the instrument in a space axially longer and wider in diameter than the sharp leading end of the instrument, and which leaves said open frustum of said hollow cone in a position overlying the trailing end of the body of the sharp instrument substantially ahead of the means whereby the sharp instrument is manipulated.

2. The conical sharps shield, as in claim 1, wherein said open apex of said hollow cone is useful for air drying or flushing decontamination of the sharp leading end of an inserted sharp instrument prior to manual extraction for cleansing or sterilization, and use again.

3. The conical sharps shield, as in claim 1, wherein the length, diameter and angle of tapering in different portions of said hollow may vary to suit the configuration of the sharp instrument to be inserted.

4. The conical sharps shield, as in claim 1, wherein a rhomboid circumferential external flange for finger grasping is located at or near said open trailing end of said frustum of said hollow cone, the precise location depending on the most efficient position for comfortably inserting, wedge impacting and shielding a given sharp instrument with one hand.

* * * * *